United States Patent [19]

Noppe et al.

[11] Patent Number: 5,491,098
[45] Date of Patent: Feb. 13, 1996

[54] METHOD FOR DEPOSITING METAL PARTICLES ON A MARKER

[75] Inventors: Marcus J. M. Noppe, Kalmthout; Frank J. Konings, Antwerpen, both of Belgium

[73] Assignee: Janssen Pharmaceutica N.V., Beerse, Belgium

[21] Appl. No.: 231,948

[22] Filed: Apr. 21, 1994

Related U.S. Application Data

[63] Continuation of Ser. No. 956,449, Oct. 2, 1992, abandoned, which is a continuation of Ser. No. 696,283, Apr. 26, 1991, abandoned, which is a continuation of Ser. No. 161,828, Feb. 29, 1988, abandoned, which is a continuation-in-part of Ser. No. 23,733, Mar. 9, 1987, abandoned.

[51] Int. Cl.$^6$ .................................................. G01N 33/553
[52] U.S. Cl. ........................ 436/525; 435/7.1; 435/7.92
[58] Field of Search .................................. 436/525, 518; 435/7.94; 424/3

[56] References Cited

U.S. PATENT DOCUMENTS

| | | |
|---|---|---|
| 3,650,748 | 3/1972 | Yudelson et al. . |
| 4,066,804 | 1/1978 | Andrews . |
| 4,204,868 | 5/1980 | Boston ................................ 430/251 X |
| 4,313,734 | 2/1982 | Leuvering . |
| 4,472,509 | 9/1984 | Gansow et al. ........................ 436/804 |
| 4,559,291 | 12/1985 | Neumann et al. .................. 430/491 X |
| 4,687,736 | 8/1987 | Newmann et al. ....................... 436/518 |
| 4,775,636 | 10/1988 | Moeremans et al. . |

FOREIGN PATENT DOCUMENTS

| | | |
|---|---|---|
| 43032/72 | 8/1972 | Australia . |
| 0165633 | 5/1985 | European Pat. Off. . |
| 0173629 | 8/1985 | European Pat. Off. . |

OTHER PUBLICATIONS

S. Nakatsuji et al., Bull. Chem. Soc. Japan, vol. 42, 3598–3600 (1969).

Nakatsuji, S. et al., Chem. Abstr. 72(14): Abstract No. 71265n (1969).

Moeremans, M., et al., Immunochemistry, vol. 102, 1985, p. 437 (No. 94024k).

Moeremans, M. et al., Chemical Abstracts, vol. 107, 1987, p. 356 (No. 3815h).

Gallyas, F., Stain Technology, vol. 54, No. 4, pp. 173–176, 1979.

*Primary Examiner*—Mary E. Ceperley
*Attorney, Agent, or Firm*—W. Scott McNees

[57] ABSTRACT

An improved method for depositing metal particles on a marker which catalyzes the reduction of metal ions from a physical developer comprising a solution of metal ions, a molar excess of complexant in respect to the metal ions and a reducing agent. Said method being preferably employed for the detection of one or more components of an aggregate formed between a least one specific binding agent and its corresponding bindable substance by labelling at least one component of said aggregate with a marker and contacting said aggregate with a physical developer, whereby under influence of the marker a metal particle is formed which can be detected. Further the invention also relates to solutions and test-kits adapted for carrying out the above mentioned method.

15 Claims, No Drawings

METHOD FOR DEPOSITING METAL PARTICLES ON A MARKER

CROSS-REFERENCE TO RELATED APPLICATIONS

This is a continuation of U.S. Ser. No. 956,449, filed Oct. 2, 1992, now abandoned; which was a continuation of U.S. Ser. No. 696,283, filed Apr. 26, 1991, now abandoned; which was a continuation of U.S. Ser. No. 161,828, filed Feb. 29, 1988, now abandoned; which was a continuation in part of U.S. Ser. No. 023,733, filed Mar. 9, 1987, now abandoned.

BACKGROUND OF THE INVENTION

Various methods are presently used for the qualitative and/or quantitative determination of specific binding agents and/or their corresponding bindable substances. Although these methods differ widely from each other in sensitivity, ease of operation and chemical and physical principles involved, important similarities are generally recognized. Typical examples of the relationship between a specific binding agent and its corresponding bindable substance(s) are of the type antigen-antibody, antibody-antigen, protein-protein, protein-ligand, receptor-ligand or nucleic acid-complementary nucleic acid. Antigen-antibody or immunological interactions are by far the most important in this connection, and particularly for diagnostic purposes, detection methods based on such interactions are the most widely used today.

Various techniques can be employed to detect and optionally quantify the aggregates, by aggregates we mean complexes formed between the specific binding agents and bindable substances involved. In certain instances, the complexation reaction will lead to a directly visible signal as a result of agglutination and/or precipitation of the aggregate itself. This will however not always be the case and, in general, the concentration of binding agent and bindable substance, needed to produce such result, will be far above the practical and useful limits. In order to circumvent this lack of sensitivity or to detect otherwise un-detectable aggregates, various methods have been developed such as, for example, complement fixation, passive haemagglutination, radio-immuno assay (RIA), immuno-fluorescence and enzyme-linked immuno sorbent assay (ELISA). In the last three methods, the detection of the aggregate is improved by labelling the aggregate with an easily detectable marker, which is either bound directly to the specific binding agent, to a secondary binding agent for which the primary binding agent acts as a bindable substance, or to the bindable substance. In the three methods listed, the marker is respectively a radioactive atom or group, a fluorescent substance or an enzyme. Such methods are described i.a. in Weir's Handbook of Experimental Immunology (1967), Blackwell Scientific Publications, Oxford and Edinburgh and U.S. Pat. No. 3,654,090 (ELISA).

During the last years, methods have been introduced wherein aggregates formed between specific binding agents and bindable substances are detected by labelling the said aggregates directly or indirectly with small sized metal particles, particularly gold particles. Depending on the circumstances, these particles can be detected, e.g. by direct visual examination, by microscopic or spectrophotometric techniques. A description of the "immunogold staining (IGS) technique", "the sol particle immuno assay (SPIA) technique" of specific applications and improvements thereof can be found e.g. in U.S. Pat. Nos. 4,313,734, 4,446,238 and 4,420,558, in U.S. Ser. No. 622,923, which corresponds to the European Patent Publication No. 165,634, in U.S. Ser. No. 660,832, which corresponds to the Eur. Pat. Publ. No. 158,746 and in IBRO handbook series, Wiley, New York, 1983, pages 347 to 372.

Metal particles have further been employed for the staining of acceptor substances, such as proteins and nucleic acid, which are directly immobilized on a solid support. Such a method is for example described in U.S. Ser. No. 744,091, which corresponds to the European Patent Publication No. 165,633.

Starting from a relatively unknown method for labelling cell surface antigens, metal particles have today become widely used in a variety of detection and/or quantitive determination problems. The possibility of direct visual examination of metal particles and the advantage that the signal generated is permanent and not prone to rapid degradation makes it an interesting marker for simple and rapid assays. Moreover metal markers, preferably gold markers, seem preferable over radioisotope markers due to the very low health hazard related to working with the former.

In the European Patent Publication No. 158,746 page 10 lines 18 to 32 there is described a method to improve the signal of a colloidal gold marker significantly by subjecting the colloidal gold particles bound to the surface of a blotting medium to a so-called physical developing procedure.

The art-known physical developers generally consist of a solution containing a soluble metal salt, such as silver nitrate, a reducing agent, such as hydroquinone and an appropriate buffer system to establish a specific pH, preferable less than pH 4.

Initially the reduction of silver ions to metallic silver is catalyzed at the surface of gold particles resulting in a specific deposition of metallic silver at the gold particle site. In turn, the thus formed metallic silver particles catalyze the reduction, creating an auto-catalytic process. The effect of a physical development is that the reddish optical gold signal turns into a deep-brown to black silver signal, with a much higher intensity. The use of these art-known physical developers results in an improved signal, although there are a number of drawbacks associated with it.

One of the major problems is the solubility of the metal salts. Indeed, it is well known that metal ions, such as silver ions, form insoluble salts with many counter ions. Apart from depleting the available silver ion supply, these insoluble salts also form nuclei at which the reduction process is catalyzed as well, which results in a seriously augmented noise level. Moreover, silver ions may form light sensitive silver salts, such as silver bromide and silver chloride, which are readily reduced to metallic silver under the influence of light, starting an auto-catalytic process. It is therefore absolutely necessary to work with extremely clean contacting surfaces, e.g. vessels, analytical grade chemicals and ultra-pure water. Usually it is also necessary to introduce multiple washing steps between the incubation with the metal-marked specific binding agent and the physical development of the marker in order to remove unwanted ions present in the incubation medium. All this tends to make traditional physically developed metal-based assays more complex, expensive and error prone.

The major disadvantage of the traditional methods lies within the nature of physical developing itself. In the case of a silver-based physical developer, for example, the reducing agent reduces all silver ions at a certain rate. To obtain optimal sensitivity the amplification process has to be aborted by removing the physical developer from the metal marker-containing phase before the non-marker-induced reduction, the so-called 'self-nucleation', becomes apparent. It is obvious that physical developers become more flexible and powerful if the ratio between metal-specific reduction speed and speed of self-nucleation can be augmented. With the traditionally used physical developers, this ratio can hardly be augmented. The only parameter which can be modulated is the overall speed of the process; self-nucleation can be postponed only at the expense of a slower metal marker amplification. One of the most obvious ways to do this is to change the concentration, nature or environment of the reducing agent. A frequently used approach is the use of hydroquinone at a pH lower than 4. The reducing action of hydroquinone is strongly inhibited in an acid environment; the user of the physical developer therefore has enough time to stop the metal marker amplification before self-nucleation causes too much noise. However, acid additions are in many cases not compatible with the nature of the binding between the marked specific binding agent and its corresponding bindable substance. Most monoclonal antibodies have only a low or average affinity to their antigens at said pH. Moreover, no real gain in sensitivity can be accomplished because the marker amplification is slowed down to the same degree as the self-nucleation is slowed down.

Thus there is a strong need for improving the sensitivity and practicality of metal based detection and/or quantitative determination techniques.

DESCRIPTION OF THE INVENTION

The present invention provides a method for depositing metal particles on a marker which catalyzes directly or indirectly the reduction of metal ions from a physical developer whereby the physical developer used comprises a solution of metal ions, a molar excess of complexant in respect to the metal ions, a reducing agent and, if desired, a buffer system and one or more adjuvants. Said method is preferably employed for qualitatively and/or quantitatively determining one or more components of an aggregate formed between at least one specific agent and its corresponding bindable substance by labelling at least one component of said aggregate with the aforementioned marker. Said preferred method can conveniently be carried out by immobilizing the specific binding agent or the corresponding bindable substance, directly or indirectly, on a solid support, contacting the support with a counterpart labelled with a marker which catalyzes the reduction of the complexed metal ions of the physical developer, and adding the physical developer before or after the separation of the bound and free labelled components, whereby during the reaction or after an adequate reaction time, the formed metal particles are quantitatively and/or qualitatively determined in the test sample and/or in the derived fractions to provide a qualitative and/or quantitative indication of the component or components to be determined. In some instances it may be preferable to contact the support containing the immobilized bindable substance with a first binding agent specific to said bindable substance to form an aggregate herewith, and subsequently contacting the support carrying the thus formed aggregate with a second binding protein, which is specific to the said first binding protein, labelled with marker. The thus described method is particularly suited for the determination of immunochemical components, such as haptens, antigens and antibodies.

Further, the present invention may also be employed for quantitatively and/or qualitatively determining an acceptor substance, such as a protein or a nucleic acid, which is directly immobilized on a solid support and bound with the aforementioned marker.

Another aspect of the present invention is to provide versatile solutions and test-kits adapted for carrying out the above mentioned methods.

The present invention remedies the drawbacks associated with the traditional developers by adding an excess of complexant to the developer. The complexants for use in the method according to the invention comprise any agent capable of forming water-soluble complexes with the metal ions of the physical developer. The complexation constant is selected so that on the one hand sufficient uncomplexed metal ions are present to allow the growth of the metal particles on the marker, while on the other hand the concentration of uncomplexed metal ions is sufficiently low to avoid the aforementioned undesirable side effects.

Useful complexants in the method according the invention have at least one nitrogen donor atom having a lone pair of electrons available on nitrogen, such as, for example, amino acids, e.g., glycine, histidine, and heterocyclic bases. Preferred heterocyclic bases are optionally substituted mono- or bicyclic bases having at least one nitrogen accommodating a lone electron pair in a $sp^2$ hybrid orbital, such as, aromatic heterocyclic ring systems containing (i) a five membered ring having two ring nitrogen atoms, e.g., imidazole, benzimidazole, pyrazole, purine and the like, with imidazole being most preferred, and (ii) aromatic heterocyclic ring systems containing a six membered ring having one ring nitrogen atom, e.g., pyridine, aminopyridine, nicotinamide, quinoline and the like. In connection with formation constants of silver complexes with imidazole and pyridine derivatives reference may be made to the Bulletin of the Chemical Society of Japan, 42, 3598–3600 (1969).

The marker for use in the method according to the invention is meant to include any particle which can catalyze the reduction of metal ions, resulting in a deposition of the corresponding metal particles at the site of the said marker. Often the thus disposed metal particles in turn catalyze the reduction, creating an autocatalytic process.

The markers to be used comprise metals, metal compounds or polymers optionally coated or impregnated with metals or metal compounds which can catalyze directly or indirectly the reduction of metal ions on their surface. As examples of such metals there may be named gold, silver, thallium, platinum, palladium as well as copper, nickel and the like with gold being preferred. As examples of metal compounds there may be named their corresponding complexes and sulfides. Polymers coated or impregnated with metals or metal compounds have similar properties as the metal or metal compounds but size, density and metal content can be optimally combined. For use in the preferred method the marker should be selected so that specific binding agents or any agent bindable thereby can be attached to the marker without loosing their affinity for their binding or bindable counterpart.

Particularly preferred markers for use in the method according to the present invention are either (i) colloidal metal particles, optionally a sol, containing metals or metal sulfides; or (ii) metal chelates, especially those incorporating ethylenediaminotetraacetic acid (EDTA) or diethylenetriaminepentaacetic acid (DTPA) groups; or (iii) polymers optionally impregnated with metals or metal sulfides, e.g., polymerization products of benzidine derivatives, such as, for example diaminobenzidine polymers.

The reducing agents for use in the method according to the present invention are meant to include any agent which reduces metal ions, preferably silver, gold, platinum, palladium or thallium ions, from a physical developer in proximity of an active site. Preferably said reducing agents form stable solutions with one or more constituents of the protected physical developer. As reducing agent there may particularly be mentioned, 1,2-dihydroxybenzene, 1,4-dihydroxybenzene (Hydroquinone), 4-methylaminophenolsulfate (Metol®), 4-aminophenol, 1,4-diaminobenzene, 1,2-diaminobenzene, N-(4-hydroxyphenyl)glycine, 2,4-diaminophenol, 1-phenyl-3-hydroxypyrazole (Phenidone®) or mixtures thereof. As other constituents (adjuvants) of the protected physical developer there may be mentioned, buffers, preservatives, e.g., anti-oxidants or organic stabilizers, speed regulators, bactericides and the like, such as, for example, sodium sulfite, sodium bisulfite, sodium citrate and the like.

The preparation of colloidal markers, in particular colloidal gold particles, their attachment to specific binding agents or any agents bindable thereby and the various methodologies of combining them, directly or indirectly, with the desired bindable substances are sufficiently known. In this connection, reference may be made to U.S. Pat. No. 4,313,784; U.S. Ser. No. 660,832 which corresponds to the European Patent Publication No. 0,158,746; U.S. Ser. No. 744,091 which corresponds to the European Patent Publication No. 0,165,633; Immunohistochemistry, Cuello, A.C. (ed.), IBRO handbook series, Wiley, New York, 1983, pages 347 to 372 and Techniques in Immunocytochemistry Vol. 2, pages 217 to 284 (1983).

In general, the attachment is easily effected by contacting the particles with an aqueous medium of appropriate pH wherein the desired binding agents, e.g., antibodies, are dissolved. In order to protect the particles from non-selective interactions with non-specific proteins of the test samples it may be appropriate to add quenching or stabilizing agents such as, for example, immunochemically inert polar macromolecules, e.g. bovine serum albumin (BSA), polyvinyl pyrrolidone (PVP) and polyethylene glycol (PEG). After a suitable period of time the unstabilized particles and free or loosely bound binding agents are removed by repeated centrifugation and washing. If desired, the particles can also be sized according to a procedure described in J. Cell Biol. 90, 533–536.

Alternatively, the proteins can also be covalently bound to the markers following the procedure described in U.S. Pat. No. 3,857,931 using a water soluble carbodiimide coupling agent.

The attachment of metal chelates to binding agents such as antibodies is easily carried out following methodologies described in for example, Analytical Biochemistry 142, 68–79 (1984) and in Cancer Research 45, 5694–5699 (1985). In general, reactions for coupling chelating agents such as diethylenetriaminepentaacetic acid (DTPA), ethylenediaminotetraacetic acid (EDTA) and the like to proteins include diazonium coupling and acylation with activated carboxyl groups. The thus obtained chelator-conjugated proteins retain their immunoreactivity and can easily be charged with the desired metallic element.

As polymers which could be used as marker for use in the methods of the present invention there may be named the polymerization products of benzidine derivatives being optionally charged with metals or metal compounds. The use and preparation of diaminobenzidine polymers is described, for example in J. Histochem. Cytochem. 30, 183–184 (1982) and Neuroscience 13, 513–525 (1984).

The determinations to be made according to the preferred method of this invention may be performed homogeneously or heterogeneously. Homogeneous determinations are particularly simple to perform but require a measurable change of the perceived signal arising from either those markers present in the labelled reagent or in the labelled aggregate formed between the labelled reagent and the particles to be determined. In those instances where no such distinction is possible, heterogenous determinations will have to be performed.

Homogeneous determinations are advantageous due to the fact that it is not necessary to physically separate the bound and unbound labelled species, thus reducing the number of steps necessary to perform an assay. The reaction between the labelled component and the corresponding binding counterpart causes the measurable change in the label's participation in or modulation of the signal generating moiety necessary to perform a homogeneous determination. The distribution of the markers between the bound and unbound species may be differentiated by the inability or altered ability of the said markers to affect the signal arising therefrom after development when present in the bound species.

A homogenous determination may conveniently be performed according to art-known procedures such as, for example, the competitive binding technique. The sample containing the analyte is combined with a binding counterpart of the analyte, a labelled reagent comprising a marker coupled to the analyte or a specific binding analogue thereof, and the physical developer necessary to convert the marker to the signal generating moiety itself. Alternatively, a sequential determination may be performed whereby the sample and the analyte binding counterpart are first combined and thereafter the detectant reagent added.

In many instances it is not possible to perform homogeneous determinations. In these cases a heterogeneous determination can be a particularly attractive alternative. In general, the heterogeneous determination system comprises at least two basic constituents and the physical developer which are combined simultaneously or subsequently, i.e. the analyte to be detected, a binding counterpart labelled with a marker and the physical developer necessary to convert the marker to the signal generating moiety itself. If necessary after an appropriate incubation period or periods the labelled reagent becomes bound to the corresponding bindable substance to be detected whereby the ratio of the bound species to the unbound species is a function of the amount of analyte being present. The bound and unbound species are physically separated and the amount of label being present in one thereof is determined.

Various means of performing the separation step and of performing the binding reactions are known in the art. The said separation may involve conventional techniques such as, for example, by employing a solid-phase antibody or antigen, a second antibody, or a solid-phase second antibody; or by the use of immuno complex precipitation agents, adsorbents, and the like. The said binding reactions may for example include the so-called competitive binding technique, the sequential saturation technique, the sandwich technique, and the like.

The preferred determinations to be made according to the method of this invention are heterogeneous determinations which are generally based on the principle that the labelled aggregate formed between the specific binding protein and the bindable substances is at some time immobilized in such manner that any unreacted particles can be washed off, whereupon the immobilized particles are detected "in situ" or, if desired, after disengagement in any other phase derived therefrom.

In a particularly preferred embodiment, the binding substance to be detected, which may be contained in a crude test specimen or in a purified or partly purified fraction derived therefrom, is immobilized on an appropriate immobilizing support prior to its complexing with the labelled binding agent, specific to said bindable substance.

The immobilization of the bindable substance may be carried out following the usual techniques, e.g., by spotting an aliquot of the test specimen on the immobilizing support or by immersing the latter in the test sample and subsequently drying and optionally washing off non-immobilized material. This is the so-called direct technique. As immobilizing supports for this technique use can be made of various materials, in general polymeric materials like, nitrocellulose, diazobenzyloxymethyl (DBH)- and diazophenylthioether (DPT) modified cellulose paper, paper, paper or cellulose acetate activated with cyanogen bromide, agarose, nylon, plastics and the like, which may take any form which is convenient for the determination process, e.g. sheets, beats, welled plates, dip-sticks and the like.

The support is then brought into contact with a labelled binding agent under conditions which allow aggregate formation between the binding agent and the corresponding bindable substances. Consequently, at the sites where the bindable substance is immobilized, markers will be immobilized in turn in amounts proportional to the concentration of the immobilized bindable substance.

In a variant of this method, the immobilized bindable substance is first allowed to react with a first binding agent which is specific therefor and subsequently the thus immobilized phase is brought into contact with the markers attached to a second binding agent which is specific for said first binding agent.

Because of the lack of selectivity and specificity of the immobilizing process as described above, the direct method is usually employed with relatively pure or purified test samples or fractions. For more complex samples, the direct method will often be less suitable, as the non-specific immobilization of a large excess of non-desired material will interfere with the sensitivity and specificity of the determination.

To avoid this problem, which is important with regard to routine analyses, an indirect or so-called sandwich technique can be used. In this technique, a purified or enriched primary specific binding agent is immobilized on a solid support. The latter is contacted with the test sample under conditions which allow the complexing of the corresponding bindable substances, which consequently become immobilized themselves. After removal of the test sample and washing of the support, the latter is contacted with a suspension of markers coated with secondary specific binding agents which are able to bind to uncomplexed sites of the immobilized bindable substance.

The most straightforward case of embodiment to which the invention is applicable is a flow-through environment consisting of bindable substance which is immobilized, directly or indirectly, to a solid phase, and a liquid phase mobile relative to the solid phase. Depending on the direction of the liquid phase flow versus the solid phase, this solid phase can be liquid-permeable or -unpermeable. For example, a permeable membrane can be used as solid phase, allowing for a perpendicular flow of the liquid phase through that membrane. On the other hand, an unpermeable solid phase can be used in combination with a lateral liquid flow.

During the first step of the embodiment, the liquid phase containing the marked specific binding agent is brought into contact with the bindable substance immobilized on the solid phase. The movement of this liquid phase relative to the solid phase may be continuous or discontinuous and must be such that the contact time between both phases allows for binding between the immobilized bindable substance and the marked specific binding agent to take place. However, this binding process not necessarily needs to reach its saturation point. The pressure drop between source and destination of the liquid phase, creating its flow, may be built in several ways. In the case of a permeable membrane as solid phase, a perpendicular flow may be created by bringing one side of this membrane into contact with a fluid-absorbing material and by applying the liquid phase on the other side. In the case of a non-permeable solid phase, a lateral flow of the liquid phase may be created by a pump.

For the second step a protected physical developer according to this invention is applied as the liquid phase. Said protected physical developer comprises complexed metal ions as well as a reducing agent. In order to maximize the ratio between marker-specific reduction speed and the speed of self-nucleation, both components are kept apart until immediatly before use. However, it should be emphasized that in comparison with the prior-art, relatively stable formulations of the physical developer can be made by mixing two stable and liquid components. In some instances it may be preferable to apply both liquid components, one comprising metal ions, a molar excess of complexant in respect to the metal ions and the other comprising a reducing agent, subsequently and thus forming the protected physical developer "in situ". In some instances, stable and liquid components may be prepared from their corresponding dry consituents by adding an appropriate amount of water. In view of the above considerations the physical developer can easily be optimized towards the marker used, the sensitivity required and the contact time between the solid phase and the liquid physical developer.

In the preferred flow-through embodiment, the mixing of the two stable liquid components and the application of the resulting protected physical developer should be combined into a single action. The application of the flowing protected physical developer has a dual effect. Initially, the liquid will wash away from the solid phase all remaining marked specific binding agents which were not or only loosely bound during the first step. Because the physical development of the marker is a gradually progressive process, this material will be washed from the solid phase before any signal becomes apparent. The remaining, bound marked specific binding agents will generate a visible signal during the further contact with the protected physical developer. The flow and volume of the developer applied to the solid phase can be chosen to ensure that the contact time is long enough for an optimal detection of the immobilized marked compounds and short enough to avoid non-specific reduction at the solid phase caused by self-nucleation. Typically, these times can be modulated from a few seconds to several minutes. For most protected physical developers there is no need for an additional treatment or fixing step to keep this signal permanent.

The advantages of this new embodiment are obvious since it offers all the advantages of the physically developed colloidal metal marker systems described earlier, but without the also described disadvantages inherent to the classical physical developers.

The present invention remedies the drawbacks associated with the classical developers by adding a molar excess of complexant to the developer preferably a several fold excess, for example, a two to a twenty fold excess. Apart from eliminating the necessity of very clean contacting surface, e.g. vessels, analytical grade chemicals, ultra-pure water and multiple pre-wash steps it also enables a severalfold increase in the ratio between marker-specific reduction speed, and speed of self-nucleation. Because the equilibrium is strongly shifted towards the complexed form, a more strongly reducing environment is allowable to mobilize the free metal ions necessary for the physical development. Under these circumstances the catalytic effect of the marker is more pronounced, resulting in an accelerated marker-specific reduction speed, without effecting the speed of self-nucleation. The increased ratio between marker specific reduction speed and the speed of self-nucleation can be exploited in several ways. In contrast with the prior art the sensitivity can be increased by keeping the marker longer into contact with the physical developer, or the speed of the marker specific development can be increased without loosing the flexibility offered by a safe period of time between the moment of optimum marker development and the moment where self-nucleation starts to give an increased background. In some cases a combination of both increased overall speed and sensitivity can be implemented. Said overall speed can easily be modulated by changing the concentration, nature or environment of the reducing agent. The utmost speed can be obtained using very small markers, preferably less than 5 nm, e.g., about 1 to 4 nm particles. In case gold particles are developed according to the present invention, the speed of the system can perfectly be modulated from very fast (10–20 sec) to slow (30 min or more). Obviously, none of the methods of the prior art can achieve such possibilities. Common developing systems only enable average (6–10 min) to low speed (15–30 min) systems. Further it should be noted that small markers not only accelerate marker-specific reduction speed but also accelerate the diffusion rate of the labelled reagents, and enable more efficient attachment of the markers to the suitable binding agents, resulting in an increased stability of the labelled reagents in suspension. Another point which should be emphasized for comparison with the prior art concerns the possibility to work in a neutral environment (pH 7) during development which results in an increased stability of the bound(s) formed between the binding pairs.

The detection of the formed metal particles in a certain phase of the reaction mixture may take place using numerous techniques which are in themselves known. Said techniques are based upon the amount and/or the physical properties of the metal particles formed, preferably on the scattering and adsorption of the metal particles. As examples of these techniques there may be cited the spectrophotometric techniques such as densitometry, which will be preferred when quantitative determinations are desired. However, in view of the high sensitivity obtained the particles can easily be observed visually, optionally using a microscope.

The specific binding agents which can be employed in the preferred method according to the invention can be of various nature but will in many instances be antibodies to specified antigens or haptens. As an example of specific binding substances other than antibodies there can be mentioned phages, which are optionally chemically or genetically adapted to bind molecular or cellular materials, lectins, which specifically bind glycoproteins, *Staphylococcus aureus* protein A which specifically binds immunoglobulins of various animal species and DNA or RNA probes for gene identification. In general any other moleculare interaction of sufficient specificity and affinity can be employed. Antibodies may be polyclonal or monoclonal.

The binding reaction of the specific binding agent(s) and bindable substance(s) will in almost all cases be allowed to proceed under mild conditions. The reaction mixture will in general be an aqueous medium with any desirable organic co-solvents being present in minor amounts. The temperature of the reaction will be maintained at a constant level in normal circumstances throughout the incubation period. Temperatures will generally be between 0° and 50° C., more usually between 20° and 40° C. Preferably the reaction will proceed at room temperature. The pH of the reaction mixture will vary between 5 and 10, more usually between 6 and 9. The concentration of various reagents will depend on the level of analyte expected in the test medium, with such level usually being between $10^{-3}$ and $10^{-12}$M. Selection of the parameters is primarily based on empirically derived optimization balanced against the preferences and needs of the technician who will ultimately perform assays on a routine basis. None of the parameters therefore is of a critical nature to the present invention, rather they are all within the ordinary ranges used in the art.

In view of their general nature, the methods according to the invention have an extremely wide field of application. In principle they can be applied to the qualitative and/or quantitative determination of any substance which can be labelled with the aforementioned marker. For example, such substances comprise but are not limited to cell surface and tissue antigens, biological substances excreted by or derived from living organisms, particularly biological substances occurring in biological fluids such as saliva, lymph, blood and its derived fractions such as, plasma and serum, urine, cerebrospinal fluid, amnion fluid, and the like. Substances which can be detected include, proteins, polypeptides, peptides, like enzymes, hormones, structural proteins, nucleic acids, vitamins, polysaccharides, toxins, alkaloids, glycoproteins, haptens, metabolites, pharmacological agents, pesticides, pollutants, steroids, and any other molecule for which a specific binding counterpart exists in biological systems or can be synthesized.

Representative protein analytes include the classes of protamines, mucoproteins, glycoproteins, globulins, albumins, scleroproteins, phosphoproteins, histones, lipoproteins, chromoproteins, and nucleoproteins. Examples of specific proteins are prealbumin, $\alpha_1$-lipoprotein, human serum albumin, $\alpha_1$-acid glycoprotein, $\alpha_1$-antitrypsin $\alpha_1$-glycoprotein, transcortin, thyroxine binding globulin, haptoglobin, hemoglobin, myoglobin, ceruloplasmin, $\alpha_2$-lipoprotein, $\alpha_2$-macroglobulin, $\beta$-lipoprotein, erythropoietin, transferin, hemopexin, fibrinogen, the immunoglobulins such as IgG, IgM, IgA, IgD, and IgE, IgG being preferred and their fragments, e.g., $F_c$, $F_{ab}$ and $F(ab)^2$ complement factors, prolactin, blood clotting factors such as fibrinogen, thrombin and so forth, insulin, melanotropin, somatotropin, thyrotropin, follicle stimulating hormone, luteinizing hormone, gonadotropin, thyroid stimulating hormone, placental lactogen, intrinsic factor, transcobalamin, serum enzymes such as alkaline phosphatase, lactic dehydrogenase, amylase, lipase, phosphatases, cholinesterase, glutamic oxaloacetic transaminase, glutamic pyruvic transaminase, and uropepsin, endorphins, enkephalins, protamine, tissue antigens, bacterial antigens, and viral antigens such as hepatitis associated antigens (e.g., $HB_sAg$, $HB_cAg$ and $HB_eAg$).

Representative hapten analytes include the general classes of drugs, metabolites, hormones, pesticides, pollutants, vitamins, and the like organic compounds. Haptenic hormones include thyroxine and triiodothyronine. Vitamins include vitamins A, B, e.g. $B_{12}$, C, D, E and K, folic acid and thiamine. Drugs include antibiotics such as aminoglycosides, e.g., gentamicin, tobramycin, amidacin, sisomicin, kanamycin, and netilmicin, penicillin, tetracycline, terramycin, chloromycetin, and actinomycetin; nucleosides and nucleotides such as adenosine diphosphate (ADP) adenosine triphosphate (ATP), flavin mononucleotide (FMN), nicotinamide adenine dinucleotide (NAD) and its phosphate derivative (NADP), thymidine, guanosine and adenosine; prostaglandins; steroids such as the oestrogens, e.g., oestriol and oestradiol, steroids; and others such as phenobarbital, phenytoin, pirimidone, ethosuximide, carbamazepine, valproate, theophylline, caffeine, propranolol, procainamide, quinidine, amitryptiline, cortisol, desipramine, disopyramide, doxepin, doxorubicin, nortryptiline, methotrexate, imipramine, lidocaine, N-acetyl-procainamide, amphetamines, catecholamines, and antihistamines. Further cardiac glycosides, and derivatives of benzodiazepine, benzimidazole, piperidine, piperazine, imidazole, triazole, pyridazine, 1,2,4-triazinedione or 2,3,5,6-tetrahydro-imidazo[ 2,1-b] thiazoles, or amides, hydratropic acid derivatives or trialkylamines.

Benzimidazole haptens comprise thiabendazole, fuberidazole, ciclobendazole, oxibendazole, parbendazole, cambendazole, mebendazole, fenbendazole, flubendazole, albendazole, oxfendazole, nocodazole and astemizole.

Piperidine haptens comprise diphenoxylate, phenoperidine, haloperidol, haloperidol decanoate, bromperidol decanoate, bromperidol, moperone, trifluperidol, pipamperone, piritramide, fentanyl, benperidol, droperidol, benzitramide, benzetimide, domperidone, sufentanil, carfentanil, alfentanil, dexetimide, milenperone, difenoxin, fluspirilene, penfluridol, pimozide, lorcainide, loperamide, astemizole, ketanserine, levocabastine, cisapride, altanserin, ritanserin, 3-[2-[4-( 4-fluorobenzoyl)-1-piperidinyl]ethyl]-2,7-dimethyl-4H-pyrido-[1,2-a]pyrimidin- 4-one, 3-[2-[4-[bis(4-fluorophenyl)methylene]-1-piperidinyl]ethyl] -2-methyl-4H-pyrido[1,2-a]pyrimidin-4-one and 3-[2-[4-[[3-(2 -furanylmethyl)-3H-imidazo[4,5-b]pyridin-2-yl]amino]-1-piperidinyl]ethyl]- 2-methyl-4H-pyrido[1,2-a]pyrimidin-4-one.

Piperazine haptens include azaperone, fluanisone, lidoflazine, flunarizine, mianserine, oxatomide, mioflazine, clocinizine and cinnarizine.

Examples of imidazole haptens are metronidazole, ornidazole, ipronidazole, tinidazole, isoconazole, nimorazole, miconazole, burimamide, metiamide, metomidate, enilconazole or imazalil, etomidate, econazole, clotrimazole, carnidazole, cimetidine, doconazole, sulconazole, parconazole, orconazole, butoconazole, triadiminole, tioconazole, valconazole, fluotrimazole, ketoconazole, oxiconazole, lombazole, bifonazole, oxmetidine, fenticonazole, tubulazole and (Z)-1-[2-chloro-2-(2,4-dichlorophenyl)ethenyl]-1H-imidazole.

Triazole haptens comprise virazole, azaconazole, etaconazole, propiconazole, penconazole, itraconazole and terconazole.

Pyridazine haptens comprise for example, 3-chloro-6-[3, 6-dihydro-4-( 3-methylphenyl)-1(2H)-pyridinyl]pyridazine, 3-methoxy-6-[4-(3-methylphenyl)- 1-piperazinyl]pyridazine and the compounds of Publ. Eur. Pat. Appl. No. 0,156,433.

1,2,4-Triazinediones comprise for example, 2-chloro-α-(4-chlorophenyl)- 4-(4,5-dihydro-3,5-dioxo-1,2,4-triazin-2(3H)-yl)benzeneacetonitrile, 2,6-dichloro-α-(4-chlorophenyl)-4-(4,5-dihydro-3,5-dioxo-1,2,4-triazin- 2(3H)-yl)benzeneacetonitrile and the compounds of Publ. Eur. Pat. Appl. No. 0,170,316.

Trialkylamines are, for example, diisopromine, prozapine. 2,3,5,6-Tetrahydro-imidazo[2,1-b]thiazoles comprise, for example, tetramisole or levamisole.

Amides comprise for example, closantel, ambucetamide, isopropamide, uzepide metiodide, dextromoramide. A hydratropic acid hapten is, for example, suprofen.

The purposes of the determinations can be multiple. In certain applications they will be used merely as a scientific tool, to visualize particular substances, e.g. on histological coupes, on chromatograms, electrophoretograms, blots, etc. For example, when applying different labels to different specific proteins or other bindable substances on a chromatogram, electrophoretogram, protein blot and the like, a reference pattern is obtained which can advantageously be used to localize other proteins or other substances. Apart from its scientific utility, the method of the invention will find utility in a wide variety of diagnostic tests such as, for example, the following: the detection and characterisation of subpopulations of T-lymphocytes; pregnancy tests based on the presence of certain hormones (chorionic gonadotropin) in the urine, diagnostic tests for various infections diseases of i.a. fungal, bacterial and in particular viral origin, such as, for example, hepatitis B, auto-immune-diseases e.g. Lupus erythromatosus and immune deficiency diseases, e.g. AIDS, gonorrhoea, rubella, poliomyelitis, and the like; diagnostics for metabolic, endocrinological and various endogenous diseases, including diagnostics for the detection of congenital malfunctions of embryos based on the presence of specific proteins in the amnion fluid.

Hence it can be employed in virtually all circumstances for which immunological techniques are conceived at present. In addition the present invention may also be employed for the determination and/or detection of acceptor substances, such as proteins or nucleic acids, which are directly immobilized in or on a solid support and bound with a colloidal marker following procedures described in the European Patent Publication No. 0,165,633 and Analytical Biochemistry 145, 315–321 (1985) which are incorporated herein as reference. Said method comprises the subsequent steps of contacting a protein or nucleic acid support for a given time, with a sufficient concentration of colloidal markers suspended in a medium, preferably containing a detergent that does not interface with protein or nucleic acid binding, like for example 0.1% of the non-ionic detergent Tween 20, and appropriately pH adjusted, and adding a physical developer whereby during the reaction or after an adequate reaction time the formed metal particles are quantitatively and/or qualitatively determined. The physical developer according to this invention improves the sensitivity of this method without the drawbacks associated with the traditional developers.

The methods according to the invention offer a framework which can be used for a wide variety of routine and experimental applications. Due to their nature and ease of handling, the methods lend themselves particularly for simple and rapid qualitative or semi-quantitative assays. These can be oriented towards use by experienced laboratory technicians as well as by non-technically trained medical personnel or laymen. The methods can also be easily automated which is an important factor when large numbers of identical determinations must be carried out, e.g., in blood banks and specialized clinical laboratories.

The invention further comprises reagent systems which comprise all of the essential chemical elements required to conduct a desired assay method encompassed by the present invention. The reagent system can be presented in a commercially packaged form, as a composition or admixture where the compatability of the reagents will allow it, in a test device configuration, or as a test kit, i.e. a packaged combination of one or more containers holding the necessary reagents. Included in the reagent system may be the reagents appropriate for the binding reaction system desired, requiring a labelled reagent and the solutions making up the protected physical developer necessary to produce the signal-generating reaction. Such binding reaction reagents can include, in addition to the labelled reagent, a binding counterpart to the analyte, and so forth. Of course, the reagent system can include other reagents as are known in the art and which may be desirable from a commercial and user standpoint, such as buffers, diluents, standards, and so forth.

More preferably the invention comprises test kits for depositing metal particles on a marker which catalyzes the reduction of metal particles on a marker which comprise, besides other reagents, a protected physical developer, which is preferably prepared by mixing two equal volumes untill immediately before use.

EXAMPLE 1

1.1 Preparation of Colloidal Gold-labelled Anti-human Immunoglobulin (Ig) Antibodies A colloidal gold sol with a mean diameter of 20 nm AuroSol G20® was purchased from Janssen Life Sciences Products, B-2340 Beerse, Belgium. Affinity-purified goat-anti-human Ig antibodies were dialyzed overnight at 4° C. against a 5 mM carbonate buffer of pH 9.8. The acidity of the gold sol was brought to pH 9.0 with potassium hydroxide. 100 ml of this gold sol was stirred in a beaker at room temperature. 1 mg of the dialyzed antibodies was added. 2 Minutes later, 1 g bovine serum albumin (BSA) was added, predissolved in 10 ml 1 μM potassium hydroxide. Another 2 minutes later, the gold-antibody-BSA mixture was centrifuged at 4° C. for 1 h at 15000 xg. After removal of the supernatant, the pellet was resuspended in 100 ml 20 mM Tris-HCl buffer at pH 8.2 containing 1% (w/v) BSA and 150 mM sodium chloride. This suspension was centrifuged again and the pellet resuspended in the same buffer to a volume at which the optical density at 520 nm was about 5.0.

1.2 Preparation of the Protected Physical Developer

Two liquid components of this developer were prepared separately. Solution A was made by dissolving 12 g histidine, 0.4 g silver nitrate and 4 g citric acid in 100 ml of distilled water. Solution B was made by dissolving 2.88 g sodium citrate, 2 g sodium sulfite, 6 g tris(hydroxymethyl)aminomethane, 0.5 g p-methylaminophenol sulfate and 0.2 g p-aminophenol.hydrochloride in 100 ml of distilled water.

1.3 Preparation of the Adsorptive Solid Phase

Squares of white nitrocellulose paper (12×12 mm) were mounted on top of and in close contact with stacks of filter paper (40×60 mm, 10 mm high). This amount of filter paper was able to absorb a few ml of water. Each nitrocellulose/filter paper stack was put in a tight cardboard box with a hole (10 mm diameter) at the site of the nitrocellulose membrane. This hole was lined with a plastic cylinder (10 mm diameter, 7 mm high). The design was such that pouring a liquid into this cylinder created a flow through the nitrocellulose membrane into the absorbing filter paper.

1.4 Performance of a Human Ig Detection in Buffer

Samples with various concentration (10 to 200 μg/ml) of human Ig were prepared in 50 mM Tris-HCl buffer of pH 8.2 containing 0.005% BSA. 5 μl of such a human Ig solution was applied at the center of the nitrocellulose membrane, leaving a wet spot of about 5 mm diameter which dried within a few seconds (antigen immobilization step). 100 μl of a 50 mM phosphate buffer of pH 7.5 containing 0.5% BSA and 0.5% Tween®20 was added to the membrane (free protein binding site saturation step). This amount of fluid covered the entire nitrocellulose membrane surface accessible through the cylinder and took about 15 seconds to flow through the membrane. 100 μl of the colloidal gold-marked anti-human Ig antibodies were added. After this volume was sucked through the membrane (another 15 seconds), 100 μl protected physical developer solution A was mixed with 100 μl solution B in a small tube. Immediately afterwards, this activated developer was added to the membrane. 30 seconds later, the developer was entirely sucked through the membrane and the experiment finished.

1.5 Results

The presence of human Ig on the membrane surface resulted in a black dot (reduced silver) at the site where the sample had been applied. Around this dot the membrane stayed white, indicating the very low level of background staining. When 5 μl of 50 μg/ml human Ig was added (250 ng), the developed signal was still clearly visible. Since not all Ig gets adsorbed this way, this corresponds to a sensitivity of better than 12 ng/mm$^2$. Starting from the immobilized antigen on the saturated membrane, the assay time took less than a minute.

EXAMPLE 2

2.1 Preparation of DTPA-coupled Human Immunoglobulins (huIg)

120 mg DTPA were heated at 50° C. for 90 minutes under stirring conditions in a mixture of 2 ml acetonitrile and 170 μl triethylamine. After cooling to room temperature, 17.65 mg N-hydroxysuccinimide and 24 μl diisopropylcarbodiimide were added and the whole was stirred for another 90 minutes at room temperature. 1 ml of the resulting DTPA conjugate was then mixed with 5 ml of a 0.1M sodium hydrogen carbonate solution at pH 7.0 containing 5 mg/ml huIg and 0.2 mM EDTA. This mixture was kept at room temperature for 60 minutes with a short shaking session every 20 minutes. After this incubation, the sample was rapidly cooled in at −20° C. for a few minutes and then kept at 4° C. Afterwards, the huIg and DTPA-huIg molecules were separated from the unreacted DTPA-conjugate by gel filtration on a Sephadex® G100 column with a 0.1M sodium acetate solution at pH 5.0.

2.2 Preparation of Silver-marked DTPA-huIg 1 ml of DTPA-huIg (optical density at 280 nm=1.0) was brought to pH 10.7 with 10 mM potassium hydroxide and drops of a 0.1M silver nitrate solution were added until the first signs of precipitation became apparent. A control sample was prepared by adding silver nitrate to DTPA-huIg at pH 5.4, conditions known to be unfavorable for the binding of silver ions by DTPA. These mixtures were incubated at room temperature for 24 hours before separation of the Ag-DTPA-huIg and DTPA-huIg molecules from the free silver ions by gel filtration on a Sephadex® G25 column with phosphate-buffered saline (50 mM phosphate buffer at pH 7.5 containing a physiological concentration of sodium chloride).

2.3 Preparation of the Protected Physical Developer

Two liquid components of this developer were prepared separately. Solution A was made by dissolving 8 g imidazole, 0.18 g silver nitrate, 1.4 g sodium citrate (.2H$_2$O) and 3.6 g citric acid (H$_2$O) in 100 ml of distilled water. Solution B was made by dissolving 3.3 g sodium citrate (.2H$_2$O), 1.5 g citric acid (H$_2$O), 1.6 g hydroquinone and 0.75 g sodium sulfite in 100 ml of distilled water.

2.4 Visualization of Ag-DTPA-huIg

Strips of white nitrocellulose paper (5×30 mm) were used as an immobilizing matrix. Two 1 µl drops of Ag-DTPA-huIg solution (optical density at 280 nm=1.0) and two 1 µl drops of DTPA-huIg control solution (see 2.2) were applied to each nitrocellulose strip as four different spots. The unsaturated protein binding sites of these strips were blocked by incubating the strips for 5 to 10 minutes in a 50 mM phosphate buffer at pH 7.5 containing 0.5% BSA (bovine serum albumin) and 0.1% Tween®20. The actual development was performed by mixing 1 ml of developer solution A with 1 ml of developer solution B in a 10 ml test tube and incubating the spotted and saturated strip in it. Development sessions were held at room temperature for 30 minutes as well as for 24 hours. After development, the strips were briefly rinsed with distilled water and air-dried.

2.5 Results

After a 30 minutes development, the Ag-DTPA-huIg spots were colored grey whereas the DTPA-huIg control spots and the background were not colored at all. After a 24 hours development, the Ag-DTPA-huIg spots were colored much more intense without any coloration of the control spots or the background. This example shows the specificity of visualizing this marker with a physical developer. Similar experiments showed that Ag-DTPA-huIg molecules have the same immunobinding behaviour as huIg molecules themselves.

3.0 Visualization of Diaminobenzidine Polymers

Strips of nitrocellulose were spotted with mouse IgG (1 µl spot, starting at 250 µg Ig/µl). After blocking for 30 minutes at 37° C. with 5% BSA the strips were incubated with goat anti-mouse IgG peroxidase labeled for 60 minutes. After 3 washings each 3 minutes with 0.05M sodium phosphate buffer pH 7.5 containing 5 g/l BSA—0.5 ml/l Tween, the strips were washed 3 times with water.

A substrate solution was prepared by dissolving 100 mg diaminobenzidine in 4 ml of a phosphate buffer (5.75 g Na$_2$HPO$_4$+1.48 g NaH$_2$PO$_4$–2 H$_2$O/l water). 0.5 ml of this solution was mixed before use with 25 ml of the same phosphate buffer and 75 µl 3% H$_2$O$_2$. The strips were developed for 9 minutes. After washing, the strips were treated for 6 minutes with 0.03% HAuCl$_4$ solution. After 3 washings 3 minutes each, the strips were sooked in a 0.142% solution of Na$_2$S. After 3 washing 3 minutes each in water, the silver enhancement was done by mixing 0.5 ml solution A and 0.5 ml solution B as described in "2.3" with 1 ml Triton X$_{100}$ solution (0.25% in H$_2$O).

3.1 Results

After 8 minutes of enhancement a strong dark (black) signal was obtained. This example clearly shows that the protected physical developer according the present invention is much more simple to use than the classical developers. In order to obtain similar results with classical developers one need several additional steps and one has to take the extreme precautions known with the use of classical developers i.e. ultrapure water glassware and the like.

We claim:

1. A method for quantitatively or qualitatively determining one or more components of an aggregate formed between at least one specific binding agent and its corresponding bindable substance which comprises labelling at least one component of said aggregate with a marker and contacting said aggregate with a physical developer whereby under influence of the marker a metal particle is formed which can qualitatively or quantitatively be determined to provide a qualitative or quantitative indication of the component or components to be determined, characterized in that the physical developer used comprises: (a) a solution of metal ions wherein said metal ions are selected from the group consisting of silver, gold, platinum, palladium and thallium ions: (b) a molar excess relative to the metal ions of a complexant having one or more nitrogen donor atoms, wherein the complexant is histidine or imidazole; and (c) a reducing agent.

2. A method according to claim 1 wherein the components of the reaction between a specific binding agent and the corresponding bindable substance are antibodies, haptens or antigens.

3. A method according to claim 1 wherein said metal ions are silver ions.

4. A method according to claim 1 wherein the marker is colloidal gold.

5. A method according to claim 1 wherein the marker is a polymerization product of a benzidine derivative.

6. A method according to claim 1 which comprises the steps of:

a) immobilizing the specific binding agent or the corresponding bindable substance directly or indirectly on a solid support;

b) contacting the support with the counterpart of the specific binding agent or corresponding bindable substance respectively, labelled with a marker which catalyzes, directly or indirectly, the reduction of the complexed metal ions from the physical developer; and c) adding the physical developer whereby during the reaction or after an adequate reaction time the formed metal particles are quantitatively or qualitatively determined in the test sample or the derived fractions to provide a qualitative or quantitative indication of the component or components to be determined.

7. A method according to claim 6 wherein the bindable substance is immobilized on the solid support by allowing the bindable substance to be bound by a specific binding agent which is immobilized on the solid support.

8. A method according to claim 6 wherein the counterpart labelled with a marker and the physical developer are part of a liquid phase which is mobile relative to the solid phase.

9. A method according to claim 6 wherein the step of adding the physical developer is performed by adding the physical developer after separation of the bound and free labelled components.

10. A method according to claim 1 which comprises the steps of a) immobilizing the specific binding agent or the corresponding bindable substance directly or indirectly on a solid support;

b) contacting the support containing the immobilized bindable substance with a first binding agent specific to said bindable substance to form an aggregate therewith;

c) contacting the support carrying the thus formed aggregate with a second binding protein labelled with a marker which catalyzes, directly or indirectly, the reduction of the completed metal ions from the physical developer, which is specific to the said first binding protein; and d) adding the physical developer whereby during the reaction or after an adequate reaction time the formed metal particles are quantitatively or qualitatively determined in the test sample or the derived fractions to provide a qualitative or quantitative indication of the component or components to be determined.

11. A method according to claim 10 wherein the first binding agent, the second binding protein labelled with a marker and the physical developer are part of a liquid phase which is mobile relative to said solid phase.

12. A method according to claim 10 wherein the step of adding the physical developer is performed by adding the physical developer after separation of the bound and free labelled components.

13. A method for qualitatively or quantitatively determining an acceptor substance which is directly immobilized on or in a solid support which comprises binding the acceptor substance with a marker and contacting said marker with a physical developer, whereby under influence of the marker a metal particle is formed which can quantitatively or qualitatively be determined to provide a qualitative or quantitative indication of the component or components to be determined, characterized in that the physical developer used comprises; (a) a solution of metal ions wherein said metal ions are selected from the group consisting of silver, gold, platinum, palladium, and thallium ions; (b) a molar excess relative to the metal ions of a complexant having one or more nitrogen donor atoms, wherein the complexant is histidine or imidazole; and (c) a reducing agent.

14. A method according to claim 13 which comprises the steps of:

a) immobilizing the acceptor substance on a solid support;

b) contacting the support with a suspension comprising a solution of colloidal markers, and at least one substance which promotes the binding of the markers to the acceptor substance;

c) adding the physical developer whereby during the reaction of after an adequate reaction time the formed particles are quantitatively or qualitatively determined.

15. A test kit for qualitatively or quantitatively determining one or more components of an aggregate formed between at least one specific binding agent and its corresponding bindable substance by labelling at least one component of said aggregate with a marker and contacting said aggregate with a physical developer, comprising a physical developer which comprises: (a) a solution containing metal ions wherein said metal ions are selected from the group consisting of silver, gold, platinum, palladium and thallium ions; (b) a molar excess relative to the metal ions of a complexant having one or more nitrogen donor atoms, wherein the complexant is histidine or imidazole; and (c) a reducing agent.

* * * * *